(12) United States Patent
Gerken et al.

(10) Patent No.: US 10,034,712 B2
(45) Date of Patent: Jul. 31, 2018

(54) CONTROL OF A MEDICAL IMAGING DEVICE VIA A NAVIGATION SYSTEM

(75) Inventors: Till Gerken, Wiesbaden (DE); Dieter Ceglarz, Munich (DE)

(73) Assignee: Brainlab AG, Munich (DE)

( * ) Notice: Subject to any disclaimer, the term of this patent is extended or adjusted under 35 U.S.C. 154(b) by 784 days.

(21) Appl. No.: 14/391,727

(22) PCT Filed: Apr. 13, 2012

(86) PCT No.: PCT/EP2012/056788
§ 371 (c)(1),
(2), (4) Date: Oct. 10, 2014

(87) PCT Pub. No.: WO2013/152803
PCT Pub. Date: Oct. 17, 2013

(65) Prior Publication Data
US 2015/0057526 A1    Feb. 26, 2015

(51) Int. Cl.
*A61B 19/00* (2006.01)
*A61B 6/03* (2006.01)
*A61B 6/00* (2006.01)
*G06F 3/0346* (2013.01)
*A61B 5/00* (2006.01)
(Continued)

(52) U.S. Cl.
CPC ........ *A61B 19/5244* (2013.01); *A61B 5/0035* (2013.01); *A61B 5/0555* (2013.01); *A61B 6/032* (2013.01); *A61B 6/037* (2013.01); *A61B 6/0407* (2013.01); *A61B 6/0457* (2013.01); *A61B 6/54* (2013.01); *A61B 6/545* (2013.01); *A61B 6/547* (2013.01); *A61B 34/20* (2016.02);
(Continued)

(58) Field of Classification Search
CPC combination set(s) only.
See application file for complete search history.

(56) References Cited

U.S. PATENT DOCUMENTS 6,814,490 B1    11/2004  Suhm et al.
2009/0278702 A1 11/2009  Graumann et al.

FOREIGN PATENT DOCUMENTS

EP    1 504 713        2/2005
WO    2011116830 A1    9/2011
WO    2012012549       1/2012

OTHER PUBLICATIONS

European Patent Office, Substantive examination for EP application No. 12714003.6 published as EP2836127A1, dated Oct. 21, 2016.
(Continued)

*Primary Examiner* — Serkan Akar
*Assistant Examiner* — Farshad Negarestan
(74) *Attorney, Agent, or Firm* — Tucker Ellis LLP (57) ABSTRACT

The present invention relates to a data processing method of determining at least one operating parameter of a medical imaging device, the method being executed by a computer and comprising the following steps:
  a) acquiring entity geometry data comprising entity geometry information describing a geometry of a corporeal entity to be considered in a medical procedure;
  b) acquiring imaging device operability data comprising imaging device operability information describing a mode of operation of the medical imaging device;
  c) determining, based on the entity geometry data and the imaging device operability data, operating parameter data comprising operating parameter information describing a value of at least one operating parameter of the medical imaging device.

7 Claims, 4 Drawing Sheets

(51) Int. Cl.
*A61B 5/055* (2006.01)
*A61B 6/04* (2006.01)
*A61B 34/20* (2016.01)
*A61B 90/00* (2016.01)

(52) U.S. Cl.
CPC ...... G06F 3/0346 (2013.01); *A61B 2090/374* (2016.02); *A61B 2090/3762* (2016.02)

(56) References Cited

OTHER PUBLICATIONS

International Search Report and Written Opinion for International Application No. PCT/EP2012/056788 dated Jan. 28, 2013.

CONTROL OF A MEDICAL IMAGING DEVICE VIA A NAVIGATION SYSTEM

RELATED APPLICATION DATA

This application is a national phase application of International Application No. PCT/EP2012/056788 filed Apr. 13, 2012 and published in the English language.

The present invention is directed to a data processing method of determining at least one operating parameter of a medical imaging device in accordance with claim 1, a corresponding computer program, computer running that program and navigation system for computer-assisted surgery comprising such a computer.

In image-guided surgery, it is desirable to reduce the number of actions to be carried out by an operator when executing an intra-operative workflow. In particular, it is desirable to reduce the number of actions which he has to conduct for controlling a medical imaging device used for providing the image guidance. By providing automatic control of a medical imaging device, complicated manual operation of the medical imaging device under sterile conditions can be avoided and costly surgical time can be reduced.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention as long as technically sensible and feasible. In particular, a feature of one embodiment which has the same or similar function of another feature of another embodiment can be exchanged. In particular, a feature of one embodiment which supplements a further function to another embodiment can be added to the other embodiment.

The present invention provides a solution to this problem in particular by acquiring input information which is associated in a specific manner with the medical procedure to be conducted as well as the technical properties of the imaging device. This input data is then used to determine at least one operating parameter of the imaging device and, according to an advantageous embodiment, for controlling the imaging device based on the value of that determined operating parameter. This allows for automatically controlling the imaging device in a manner suitable for conducting the envisaged procedure.

Preferably, the inventive method is at least partly executed by a computer. That is, all steps or just some of the steps (i.e. less than a total number of steps) of the inventive method may be executed by a computer.

Preferably, entity geometry data is acquired which comprises entity geometry information. Preferably, the entity geometry data is acquired based on data processing performed by a navigation system as described further below. The entity geometry information describes or represents in particular a geometry of an in particular corporeal entity to be considered in a medical procedure. The medical procedure in particular is the envisaged medical procedure, according to the requirements of which the imaging device shall be controlled. Such a medical procedure in particular is associated with image-guided surgery, radiotherapy, diagnostics or treatment, in particular treatment of a tumour with pharmaceuticals. The inventive method therefore is designed for use in the framework of at least one of such procedures, wherein of course such procedures may also be combined, the method therefore being designed to be used in the framework of at least one such procedure.

The entity preferably is a corporeal entity, i.e. the entity is or represents a physical structure and in particular is tangible. The entity preferably is or represents an anatomical body part, such as part of a patient's body which is subjected to the envisaged medical procedure. Alternatively or additionally, the entity may represent any other physical structure such as a medical device or instrument, respectively. The entity geometry information in particular describes the geometry of the entity, more particularly the geometry of the physical structure of the entity itself and alternatively or additionally, the position, i.e. location and orientation, of the entity in a global (operation room) coordinate system in which the entity is able to move. The orientation of the entity is preferably described by a perspective towards the entity from a tracking location outside the entity, the tracking location preferably being represented by the position of a camera used for marker-based tracking of the entity, in particular by a perspective from the camera towards the entity when tracking the entity.

In particular if the entity is an anatomical body part, the entity geometry data is acquired based on medical image data which is acquired by applying at least one medical imaging method to the respective anatomical body part. Thereby, the entity geometry information may describe or represent the internal physical structure of the entity, in particular of the anatomical body part. In the field of medicine, imaging methods (in particular, medical imaging methods) are used to generate image data (for example, two-dimensional or three-dimensional image data) of anatomical structures (such as soft tissues, bones, organs, etc.) of the human body. Medical imaging methods are understood to mean advantageously apparatus-based imaging methods (so-called medical imaging modalities and/or radiological imaging methods), such as for instance computed tomography (CT) and cone beam computed tomography (CBCT; in particular volumetric CBCT), x-ray tomography, magnetic resonance tomography (MRT or MRI), conventional x-ray, sonography and/or ultrasound examinations, and positron emission tomography. Analytical devices are in particular used to generate the image data in apparatus-based imaging methods. The imaging methods are in particular used for medical diagnostics, to analyse the anatomical body in order to generate images which are described by the image data. The imaging methods are in particular used to detect pathological changes in the human body.

The entity geometry information alternatively or additionally describes or represents a trajectory of the entity, in particular of an instrument, in particular a trajectory in a space lying in at least one of the exterior and interior of a patient's body. The trajectory is preferably described by a plurality of positions, in particular locations, which the entity, in particular instrument, has at consecutive points in time. Information about such locations is preferably acquired by an optical tracking system which acquires information about the position of the instrument by electromagnetic tracking, i.e. acquiring electromagnetic signals reflected from markers having a predetermined and preferably fixed position relative to the instrument, or by image analysis in which image features representing the entity, in particular instrument, are determined and evaluated in order to determine the position of the entity. In such cases, the entity, in particular instrument, preferably is located outside, i.e. in the exterior of a patient's body, which patient is to be subjected to the envisaged medical procedure. If the entity, in particular instrument, is located inside, i.e. in the interior of the patient's body, information about the trajectory is preferably acquired by applying at least one medical imaging method to the patient's body and the entity, in particular instrument, in order to determine the position of the entity inside the patient's body at consecutive points in time.

It is the function of a marker to be detected by a marker detection device (for example, a camera or an ultrasound receiver or analytical devices, like CT or MRI), such that its spatial position (i.e. its spatial location and/or alignment) can be ascertained. The detection device is in particular part of a navigation system. The markers can be active markers. An active marker can for example emit electromagnetic radiation and/or waves, wherein said radiation can be in the infrared, visible and/or ultraviolet spectral range. The marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can also, however, exhibit a cornered—for example, cubic—shape.

A marker device can for example be a reference star or a pointer or one marker or more than one (individual) markers which are preferably in a predetermined spatial relationship. A marker device comprises one, two, three or more markers which are in case of two or more markers in a predetermined spatial relationship. This predetermined spatial relationship is in particular known to a navigation system and for example stored in a computer of the navigation system.

A "reference star" refers to a device with a number of markers, advantageously three markers, attached to it, wherein the markers are (in particular detachably) attached to the reference star such that they are stationary, thus providing a known (and advantageously fixed) position of the markers relative to each other. The position of the markers relative to each other can be individually different for each reference star used within the framework of a navigated medical procedure, in order to enable the corresponding reference star to be identified by a surgical navigation system on the basis of the position of the markers relative to each other. It is therefore also then possible for the objects (for example, instruments and/or parts of a body) to which the reference star is attached to be identified and/or differentiated. In a navigated medical procedure, the reference star serves to attach a plurality of markers to an object (for example, a bone or a medical instrument) in order to be able to detect the position of the object (i.e. its spatial location and/or alignment). Such a reference star in particular comprises a way of being attached to the object (for example, a clamp and/or a thread) and/or a holding element which ensures a distance between the markers and the object (in particular in order to assist the visibility of the markers to a marker detection device) and/or marker holders which are mechanically connected to the holding element and which the markers can be attached to.

Preferably, the entity geometry information describes or represents a position of the entity, which entity in particular comprises or consists of an instrument and/or an anatomical body part of a patient's body, relative to at least one of the medical imaging device and the detection device of navigation system. In particular, the entity is an anatomical body part or an instrument, in particular a medical instrument, i.e. an instrument for use in a medical procedure. The relative position is preferably determined based on optical and/or electromagnetic tracking of the entity and preferably also the medical imaging device.

Preferably, the entity geometry data is associated with, i.e. is part of or comprises, treatment plan data comprising treatment plan information. In that case, the treatment plan data is preferably acquired by the inventive method. The treatment plan information describes in particular at least one of the geometry of a target region or a critical region (in particular in or on an anatomical body part of a patient to be subjected to the envisaged medical procedure, in particular in the case of therapy by application of electromagnetic radiation—radiotherapy—or pharmaceuticals, in particular for treatment of tumors), an instrument trajectory in particular inside the patient's body, a dose value to be administered to a patient's body (in particular in the case of the envisaged medical procedure being a radiotherapeutic procedure or treatment by pharmaceuticals), a pharmaceutical to administer a patient's body (in particular, in case the envisaged medical procedure involves tumor treatment by application of pharmaceuticals) and a ray geometry to be emitted by the medical imaging apparatus (in particular, in the case of radiotherapy).

According to a preferable embodiment of the invention, the entity geometry information alternatively or additionally describes or represents physical characteristics of the anatomical body part which is to be subjected to the envisaged medical procedure. For example, the entity geometry information represents or describes at least one tissue type or region type (for example, a target region which shall be irradiated or a critical region which shall rather not be irradiated). Based on such information, the operating parameter data can be determined in order to control the medical imaging device accordingly. For example, the energy to be emitted during irradiation and/or the dose to be applied to the anatomical body part can be adjusted to fit the tissue type or region type. In particular, the navigation system is able to match an atlas-based or pre-planned object to a location in space and instruct the scanner to scan just this area. The object can be determined based on the information about tissue types or region types.

An atlas typically consists of a plurality of generic models of objects, wherein the generic models of the objects together form a complex structure. The atlas of a femur, for example, can comprise the head, the neck, the body, the greater trochanter, the lesser trochanter and the lower extremity as objects which make up the complete structure. The atlas of a brain, for example, can comprise the telencephalon, the cerebellum, the diencephalon, the pons, the mesencephalon and the medulla as the objects which make up the complex structure. One application of such an atlas is in the segmentation of medical images, wherein the atlas is matched to medical image data, and the image data are compared with the matched atlas in order to assign a point (a pixel or voxel) of the image data to an object of the matched atlas, thereby segmenting the image data into objects.

Preferably, imaging device operability data is acquired which comprises imaging device operability information. The imaging device operability information in particular describes a mode of operation of the medical imaging device.

The medical imaging device preferably is a scanner, in particular a scanner for at least one of X-ray tomography, magnetic resonance tomography, conventional x-ray imaging and positron-emission tomography. The medical imaging device in particular is an analytical device which is configured to conduct an imaging method in accordance with the above definition.

The imaging device operability information in particular describes or represents a kind of imaging method to be applied by the medical imaging device and/or the types of operating parameters which can in principle be controlled when operating the medical imaging device.

Furthermore, the imaging device operability information alternatively or additionally describes or represents a medical procedure to be carried out by using the imaging device, in particular it describes the kind of envisaged medical procedure as described above. Information about the kind of imaging method, types of operating parameters and in particular envisaged medical procedure is also termed information about a mode of operation of the medical imaging device. In particular, the device operability information describes (more particularly, is) a set of operating parameters, i.e. a set of quantities (more particularly, physical quantities) which can be controlled, in particular are adjustable, and characterize a mode of operation of the medical imaging device.

Preferably, operating parameter data is determined based on the entity geometry data (in particular, the entity geometry information) and the imaging device operability data (in particular, based on the imaging device operability information). The operating parameter data in particular comprises operating parameter information which in particular describes or represents a value of at least one operating parameter of the medical imaging apparatus (in the following also called determined operating parameter). Further preferably, determining the operating parameter data comprises determining, in particular selecting, from the set of quantities, in particular operating parameters, described by or contained in the device operability information, at least one operating parameter which is to be controlled, in particular adjusted. Preferably, the value of the determined operating parameter is a value according to which the medical imaging device is operated, in particular controlled. In particular, the operating parameter is set and/or adjusted to have that value. The operating parameter is at least one of x-ray tube voltage, x-ray tube current, pitch, surface dose or effective dose to be applied, gantry tilt (in particular, relative to the surface of a patient bed and/or a frontal plane running parallel to a cranio-kaudal direction of a patient's body), position and/or size of scan volume, layer thickness of a tomographic slice (i.e. slice thickness), distance between tomography slices, at least one image reconstruction parameter (in particular filter kernel or reconstruction algorithm), and windowing. The term of pitch is considered to be standard technical terminology which denotes the ratio between movement of a patient bed and rotation of the gantry in particular during operation of a CT or MR scanner. The term of pitch therefore characterizes the degree of overlap of imaging regions, in particular slices, of helical scans. The term of reconstruction parameter in particular denotes a filter kernel or reconstruction algorithm used for reconstructing the image from the medical image data acquired by the medical imaging device. The term of windowing denotes windowing of the medical image data. Windowing describes in particular re-normalizing an image contrast onto a range of colour values which is smaller than the range of colour values in the originally acquired image data. For example, the medical image data acquired by the medical imaging device may comprise 256 colour values. When applying windowing to such medical image data, specific values are selected from those 256 colour values. The specific (selected) colour values are then used for display in particular only a specific (selected) part of the medical image data, more particularly a specific (selected) image region. The other colour values are then set to fix values, in particular to black and/or white colour values. The gantry tilt may also be virtually controlled, in particular adjusted, in particular by data processing means. In such a case, the gantry is actually not physically moved. Rather, the medical image data are geometrically transformed such that they represent an image taken at a specific tilt angle of the gantry. The surface or effective dose to be applied in particular is a radiation dose to be applied to an anatomical body part. The gantry tilt preferably is defined relative to a longitudinal axis or plane, respectively, of a patient's body who is to be subjected to the envisaged medical procedure. The scan volume in particular defines a two-dimensional or three-dimensional volume of the patient's body who is to be subjected to the envisaged medical procedure.

Preferably, the medical imaging device is controlled according to the value of the determined operating parameter. Further preferably, a signal is issued in particular by the computer of a navigation system for computer-assisted surgery as described below, which signal comprises information which indicates whether the medical imaging device has been controlled according to the value of the determined operating parameter. For example, the medical imaging device is controlled to have at least one of an x-ray tube voltage, x-ray tube current, pitch, emitted dose, and a gantry tilt to produce at least one of a scan volume, layer thickness of a tomography slice and a distance between tomography slices as indicated by the value of the determined operating parameter.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements and optionally a volatile memory (in particular, a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The present invention is also directed to a navigation system for computer-assisted surgery. This navigation system preferably comprises the aforementioned computer for processing the data provided in accordance with the data processing method as described in any one of the preceding embodiments. The navigation system preferably comprises a detection device for detecting the position of at least one of the medical imaging device, an anatomical body part and an instrument. In order to generate detection signals and to supply the generated detection signals to the computer such that the computer can acquire information about the position of the at least one of the medial imaging device, anatomical body part and instrument on the basis of the detection signals received. The navigation system also preferably comprises a user interface for receiving the calculation results from the computer. The user interface provides the received data to the user as information. The received data is generated by the computer on the basis of the results of the processing performed by the computer. Examples of a user interface include a monitor or a loudspeaker. The user interface can use any kind of indication signal (for example a visual signal, an audio signal and/or a vibration signal).

A navigation system, in particular a surgical navigation system, is understood to mean a system which comprises in particular: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) in particular comprises a processor (CPU), a working memory, advantageously an indicating device for issuing an indication signal (for example, a visual indicating device such as a monitor and/or an audio indicating device such as a loudspeaker and/or a tactile indicating device such as a vibrator) and advantageously a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

The method in accordance with the invention is in particular a data processing method. The data processing method is preferably performed using technical means, in particular a computer. The data processing method is in particular executed by or on the computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing" which describes computation, software, data access and storage services which do not require the end user to know the physical location and/or configuration of the computer delivering a specific service. In particular, the term "cloud" is used as a metaphor for the internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer.

The expression "acquiring data" encompasses in particular (within the framework of a data processing method) the scenario in which the data are determined by the data processing method or program. Preferably, the data which are acquired have been generated beforehand, further preferably they are generated outside of the claimed method, i.e. they are predetermined. In particular, the data to be acquired are generated outside of the step of acquiring, more particularly before the step of acquiring is executed. Determining data in particular encompasses measuring physical quantities and transforming the measured values into in particular digital data and/or computing the data by means of a computer, in particular computing the data within the method of the invention. The meaning of "acquiring data" in particular also encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. The acquiring step in particular does not involve an invasive step which would represent a substantial physical interference with the body requiring professional medical expertise to be carried out and entailing a substantial health risk even when carried out with the required professional care and expertise. Acquiring, in particular determining, data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe which is preferably called "XY information".

The present invention provides the following improvements to a medical imaging workflow in particular due to the employment of a navigation system, i.e. by acquiring data which is received from a navigation system:

Entering information into the scanner which is used in particular for controlling the scanner is simplified.

Definition of a scan area in two or three dimensions is made simpler and more precise.

A scout scan which is conventionally used for checking the position of the medical imaging device relative to an anatomical body part is rendered superfluous. Thereby, radiation exposure of the patient can be reduced.

Control of the imaging device takes place as part of the clinical workflow, the requirements of which may therefore be considered during control.

In particular by improving positioning of the medical imaging device relative to the anatomical body part, both identification of a surgical target and detection of fractures is rendered more reliable.

Generally and compared to conventional methods, the inventive method provides more information to an operator, provides the information more quickly and enables a quicker control of the medical imaging device.

The inventive method preferably comprises only steps of data processing. In particular, the inventive method does not comprise or encompass an invasive step representing a substantial physical intervention on the (human or animal) body which requires professional medical expertise to be carried out and which entails a substantial health risk even when carried out with the required professional care and expertise. Furthermore, the inventive method does not imply or necessitate any surgical intervention on the (human or animal) body and the inventive method may be executed irrespective or whether a surgical procedure is envisaged or not following execution of the inventive method. The inventive method does not necessitate execution of a surgical method after execution of the inventive method has finished.

In the following, the invention will be described with reference to the figures which describe embodiments without limiting the invention to the contents of the specific figure and corresponding description, wherein.

Figure 1:
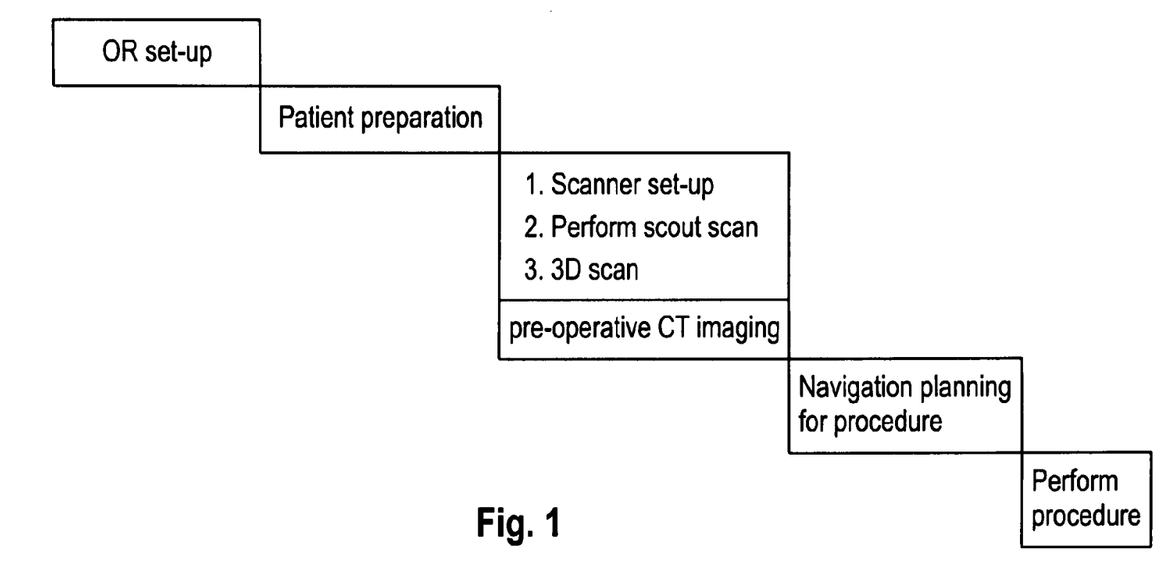
FIG. 1 shows a conventional workflow for preparing a navigated medical procedure.

According to FIG. 1, a conventional workflow for preparing a navigation-assisted medical procedure comprises steps of operation room set-up, patient preparation, pre-operative CT imaging, navigation planning for the procedure and preferably performing the procedure. The step of pre-operative CT imaging is used for acquiring in particular information about the present configuration of the scanner (scanner set-up), image data representing a scout scan (i.e. in particular a preliminary check for proper positioning of the patient relative to the medical imaging device, in particular when lying on a bed after being positioned for conducting the envisaged medical procedure) and conducting a three-dimensional scan in particular if the scout scan reveals that the patient is properly positioned. These steps of pre-operative CT imaging are associated with a comparably high radiation dose for the patient. It is therefore desirable to accelerate conducting these steps and to reduce the number of steps of pre-operative CT imaging as far as possible.

Figure 2:
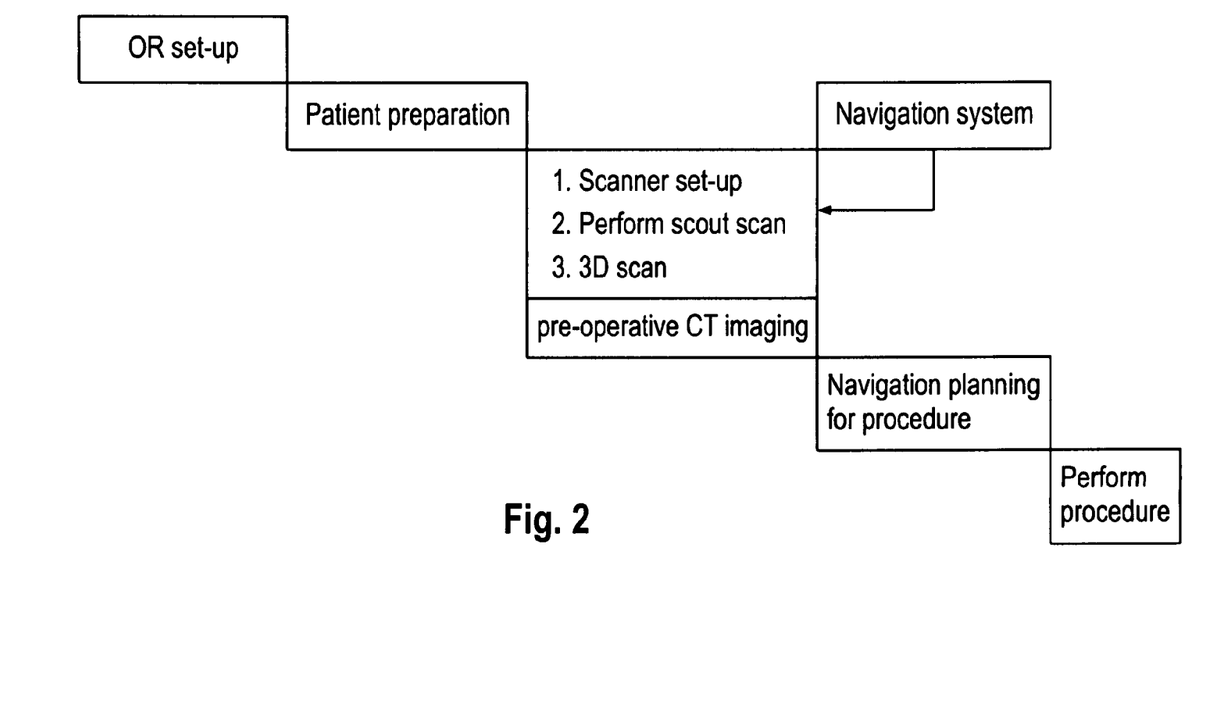
FIG. 2 shows a workflow for preparing a navigated medical procedure in accordance with the invention.

In view of such a need, the present invention provides an improved workflow which is shown in FIG. 2. The steps of FIG. 2 are essentially the same as those shown in FIG. 1 with the exception that the steps of pre-operative CT imaging are controlled by using a navigation system, in particular based on data acquired from a navigation system. As described above, the navigation system provides the entity geometry data to the inventive method in order to accelerate at least the step of scanner set-up.

Figure 3A:
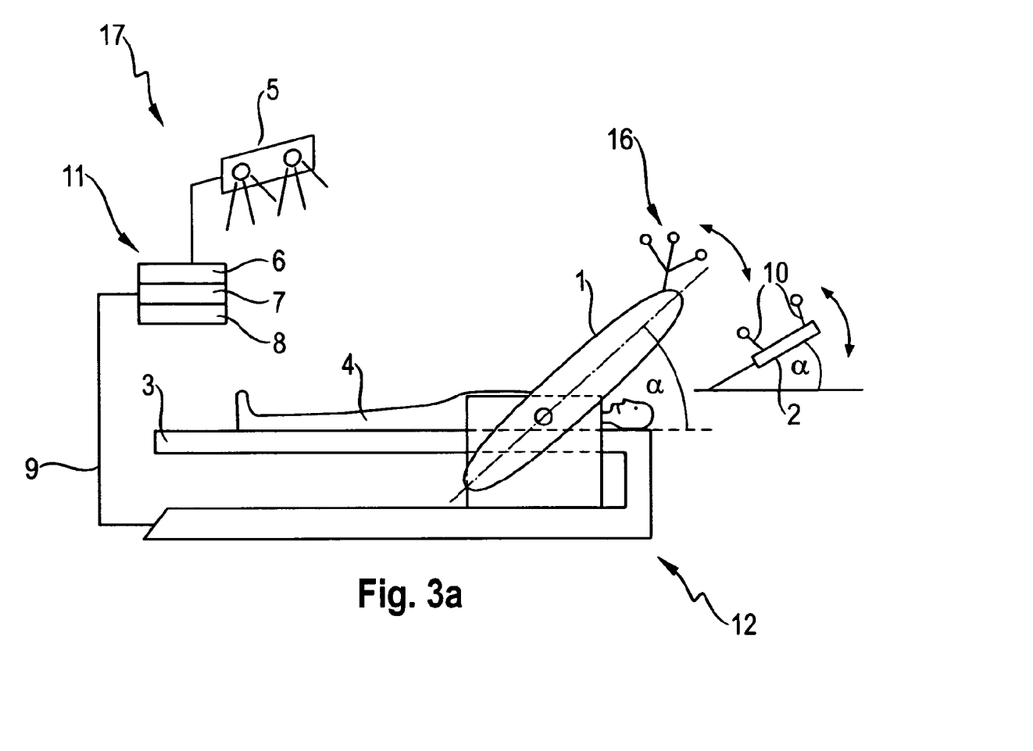
FIGS. 3a and 3b show two embodiments of determining the operating parameter data based on instrument trajectories or gestures, respectively.

FIG. 3a illustrates an embodiment of controlling the tilt angle α of a gantry 1 of a CT scanner 12 relative to a plane in which a patient 4 lies on a bed 3 of the scanner 12. The tilt a is controlled by tracking the trajectory of a pointer 2 which is associated with markers 10. Preferably, the gantry 1 is associated with a marker device (reference star) 16. The markers 10 and the marker device 16 are tracked by a navigation system 17 comprising a computer 11 and a stereoscopic camera 5 which is operatively coupled to the computer 11 having a processor 6, random access memory 7 and non-volatile memory 8. The computer 11 is operatively coupled via data link 9 to the scanner 12. Preferably, the trajectory of the pointer 2 represents a gesture formed with the pointer 2 by manual user operation. The pointer 2 is an example of a medical instrument. Preferably, each desired movement of the gantry 1 is associated with a specific gesture of the pointer 2. Further preferably, the gesture of the instrument 2 runs in the same direction as the desired movement of the gantry 1. For example, if the pointer is moved in an upward direction by the angle α, the gantry 1 is controlled in particular by signals issued by the computer 11 to be moved in the upward direction by the same angle α.

Figure 3B:
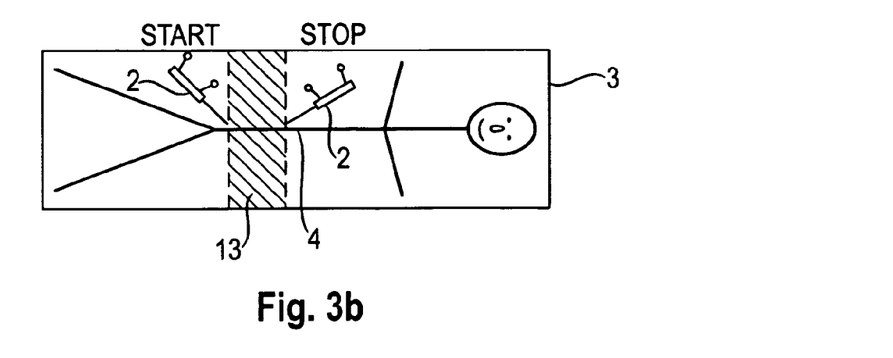

FIG. 3b shows an embodiment directed to determining a preferably two-dimensional scan area 13 along the longitudinal axis of a patient's body 4. In this example, a tracked pointer 2 points in the direction of the head end of the bed 3 on which the patient 4 is lying which is recognized as a start position of the scan area. Holding the pointer 2 in the direction of the foot end of the bed 3 is then interpreted by the navigation system to denote the stop end of the scan area 13. In this example, the scanner 12 is controlled to in particular move the patient relative to the gantry 1 (or vice versa, respectively) such that the radiation emitted from the gantry 1 images the scan area 13, the extent of which defined by the gestures of the pointer 2. Therefore, the example of FIG. 3b shows a further embodiment of controlling the medical imaging device by positioning a medical instrument.

Figure 4:
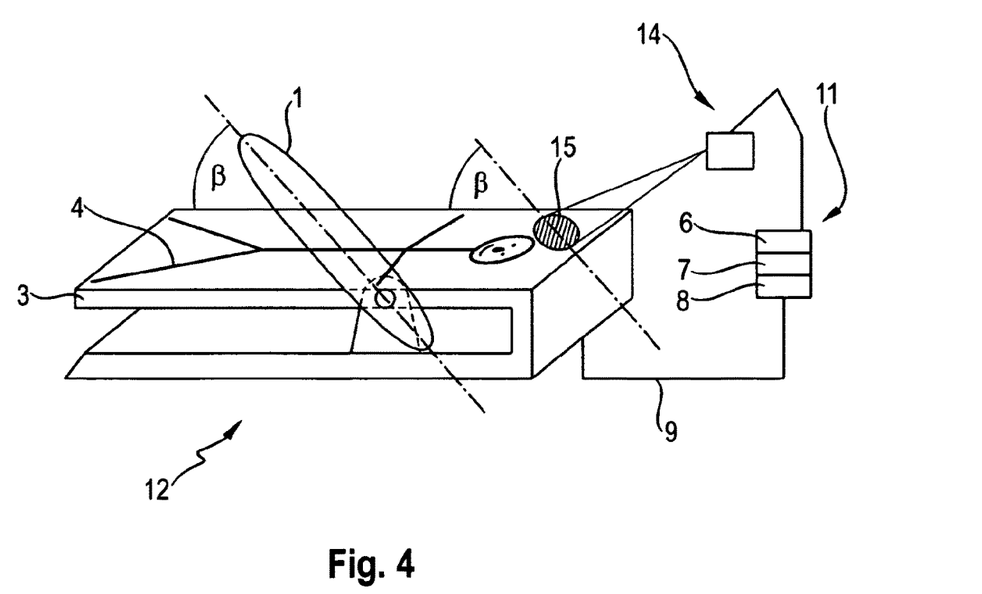
FIG. 4 shows an embodiment directed to adapting the gantry tilt to the focal plane of a microscope to be used in the medical procedure.

FIG. 4 shows a further embodiment of controlling the tilt angle β of the gantry 1 according to the position of a medical instrument which in this case is embodied by a microscope 14. The microscope 14 is operatively coupled to a computer 11 comprising a processor 6, random access memory 7 and non-volatile memory 8. The computer 11 is operatively coupled by a data link 9 with a CT scanner 12 comprising a bed 3 (on which a patient 4 is placed) and a pivotably mounted gantry 1. The microscope 14 may for example be used to image an anatomical body part which is the subject of a medical procedure. The microscope 14 has a preferably adjustable focal plane 15 which in particular depends on the position of the microscope 14 relative to the object (anatomical body part) to be imaged by the microscope 14. Preferably, the scanner 12 is used to image the anatomical body which is also imaged by the microscope 14. To this end, it is preferable that the gantry 1 (in particular, the radial plane of the gantry) is tilted parallel to the focal plane 15 in order to provide a medical image from the same perspective as the microscope 14 does. This reduces the computational effort otherwise spent for transforming the medical image data into the perspective of the microscope 14. The computer 11 preferably is a controlling instance for the scanner 12 and acquires information about the tilt angle β of the gantry 1. At the same time, the computer 11 is able to determine the position, in particular orientation, of the focal plane 15 relative to the patient 4 or the bed 3, respectively. Preferably, the computer 11 controls the gantry 1 such that its tilt angle β relative to the patient 4 or the bed 3, respectively, is the same as the tilt angle β of the focal plane 15 relative to the patient 4 or the bed 3, respectively.

According to a further embodiment of the invention, a scan area such as the scan area 13 shown in FIG. 3b can be determined based on touch-screen input. The navigation system will then calculate the spatial coordinates of the actual scan volume. Preferably, the scanner, in particular the gantry 1, is associated with a marker device such as a reference star 16 so that it can be tracked. The navigation system is then able to localize an area to be re-scanned upon request by an operator via the touch-screen input. Furthermore, the navigation system is able to localize the scanner, in particular the gantry 1, in space and can then instruct the scanner 12 to image the desired image volume along the scan area 13.

According to another embodiment, a medical instrument may be tracked in the interior of the patient's body 4 by applying a medical imaging method such as a computed x-ray tomography or a magnetic resonance imaging method. For example, biopsies are typically performed in a CT or MR scanner. The biopsy needle is moved along a preplanned image slice so that its trajectory can be followed. Presently, it is common to align the biopsy needle to a target inside the patient and then create a correct imaging volume for this trajectory. By using a navigation system, the navigation system can calculate the current trajectory of the instrument and align the scanner or its scanning volume automatically to fit that trajectory. For the case of the scanner being a CT scanner, there is the additional benefit of radiation reduction of the surgeon as it would be easy to calculate a trajectory that excludes the surgeon's hand.

The invention claimed is:

1. A data processing method for determining at least one operating parameter of a medical imaging device having a gantry, the method being executed by a computer and comprising:
   a) acquiring entity geometry data regarding a microscope comprising entity geometry information describing a geometry of the microscope having an adjustable focal plane and being a corporeal entity to be considered in a medical procedure, the focal plane having a tilt angle relative to an associated patient's body, wherein the entity geometry data has been acquired by tracking the microscope and the medical imaging device with a navigation system, wherein the entity geometry data is associated with
   treatment plan data comprising treatment plan information describing at least one of a geometry of a target region or a critical region, an instrument trajectory, a dose value to be administered to the associated patient's body, a pharmaceutical to be administered to the associated patient's body and a ray geometry to be emitted by the medical imaging device;
   b) acquiring imaging device operability data comprising imaging device operability information describing a mode of operation of the medical imaging device;
   c) determining, based on the entity geometry data and the imaging device operability data, operating parameter data comprising operating parameter information describing a value of at least one operating parameter of the medical imaging device, the at least one operating parameter including a tilt angle of the gantry relative to the associated patient's body, the tilt angle of the gantry relative to the associated patient's body being the same as the tilt angle of the focal plane relative to the associated patient's body; and
   d) controlling the medical imaging device to adjust the tilt angle of the gantry to be the same as the tilt angle of the focal plane relative to the associated patient's body.

2. The method according to claim 1, wherein the medical imaging device is a scanner for at least one of X-ray tomography, magnetic resonance tomography, conventional X-ray imaging and positron-emission tomography.

3. The method according to claim 1, wherein the operating parameter further includes at least one of X-ray tube voltage, X-ray tube current, pitch, surface dose or effective dose to be applied, position and/or size of scan volume, layer thickness of a tomography slice, distance between tomography slices, filter kernel, and windowing.

4. The method according to claim 1, further comprising issuing a signal comprising information that indicates whether the medical imaging device has been controlled according to the value of the determined operating parameter.

5. A non-transitory computer readable storage medium storing computer program for determining at least one operating parameter of a medical imaging device having a gantry, which, when running on a computer or when loaded onto a computer, causes the computer to:

a) acquire entity geometry data regarding a microscope comprising entity geometry information describing a geometry of the microscope having an adjustable focal plane and being a corporeal entity to be considered in a medical procedure, the focal plane having a tilt angle relative to an associated patient's body, wherein the entity geometry data has been acquired by tracking the microscope and the medical imaging device with a navigation system, wherein the entity geometry data is associated with treatment plan data comprising treatment plan information describing at least one of a geometry of a target region or a critical region, an instrument trajectory, a dose value to be administered to the associated patient's body, a pharmaceutical to be administered to the associated patient's body and a ray geometry to be emitted by a medical imaging device;

b) acquire imaging device operability data comprising imaging device operability information describing a mode of operation of the medical imaging device;

c) determine, based on the entity geometry data and the imaging device operability data, operating parameter data comprising operating parameter information describing a value of at least one operating parameter of the medical imaging device, the at least one operating parameter including a tilt angle of the gantry relative to the associated patient's body, the tilt angle of the gantry relative to the associated patient's body being the same as the tilt angle of the focal plane relative to the associated patient's body; and d) control the medical imaging device to adjust the tilt angle of the gantry to be the same as the tilt angle of the focal plane relative to the associated patient's body.

6. A navigation system for computer-assisted surgery, comprising:

the computer according to claim 5, the computer being configured to process the entity geometry data, the imaging device operability data, and the operating parameter data;

a detection device for detecting the position of at least one of the medical imaging device, an anatomical body part and the microscope, the detection device configured to provide the entity geometry data;

a data interface for receiving the entity geometry data from the detection device and for supplying the entity geometry data to the computer; and a user interface for receiving data from the computer in order to provide information to a user, wherein the received data is generated by the computer on the basis of the results of the processing performed by the computer.

7. A computer comprising the non-transitory computer readable storage medium according to claim 5.

* * * * *